United States Patent [19]
Unruh

[11] Patent Number: 5,928,173
[45] Date of Patent: *Jul. 27, 1999

[54] TURF TOE BRACE

[75] Inventor: Gregory J. Unruh, Olathe, Kans.

[73] Assignee: Cramer Products, Inc., Gardner, Kans.

[ * ] Notice: This patent is subject to a terminal disclaimer.

[21] Appl. No.: 08/990,947

[22] Filed: Dec. 15, 1997

Related U.S. Application Data

[63] Continuation of application No. 08/745,018, Nov. 7, 1996, Pat. No. 5,772,621.

[51] Int. Cl.⁶ .................................................. A61F 5/00
[52] U.S. Cl. ................................................. 602/30; 602/65
[58] Field of Search .................................. 602/5, 22, 30, 602/31, 27, 61–63, 65, 66; 128/845, 882, 892–894; 601/27; 2/22

[56] References Cited

U.S. PATENT DOCUMENTS

| | | |
|---|---|---|
| Re. 34,753 | 10/1994 | Groiso . |
| 826,515 | 7/1906 | Litch . |
| 1,788,852 | 1/1931 | Arthur . |
| 2,033,609 | 3/1936 | Budin . |
| 2,596,038 | 5/1952 | Mayer . |
| 3,049,120 | 8/1962 | Marcus . |
| 4,632,103 | 12/1986 | Fabricant et al. . |
| 4,637,381 | 1/1987 | Jungmann . |
| 4,644,940 | 2/1987 | Nakamura . |
| 4,729,369 | 3/1988 | Cook . |
| 4,745,927 | 5/1988 | Brock . |
| 5,010,878 | 4/1991 | Kline et al. . |
| 5,139,479 | 8/1992 | Peters . |
| 5,453,083 | 9/1995 | Kasahara . |
| 5,472,414 | 12/1995 | Detty . |

*Primary Examiner*—Linda C. M. Dvorak
*Attorney, Agent, or Firm*—Litman, Kraai & Brown L.L.C.; John McMahon

[57] ABSTRACT

A turf toe brace includes a flexible boot adapted for snugly anchoring the brace to a foot of a user, an elongate generally non stretchable strap releasably joinable in a multiplicity of configurations to the boot by a fastening mechanism and a toe loop. The toe loop is joined to the strap opposite the boot. In use the strap passes under the foot and is connected to at least one side of the boot in such a manner as to pull downwardly on the great toe and help prevent hyperextension of the great toe, especially during work or athletic events.

11 Claims, 1 Drawing Sheet

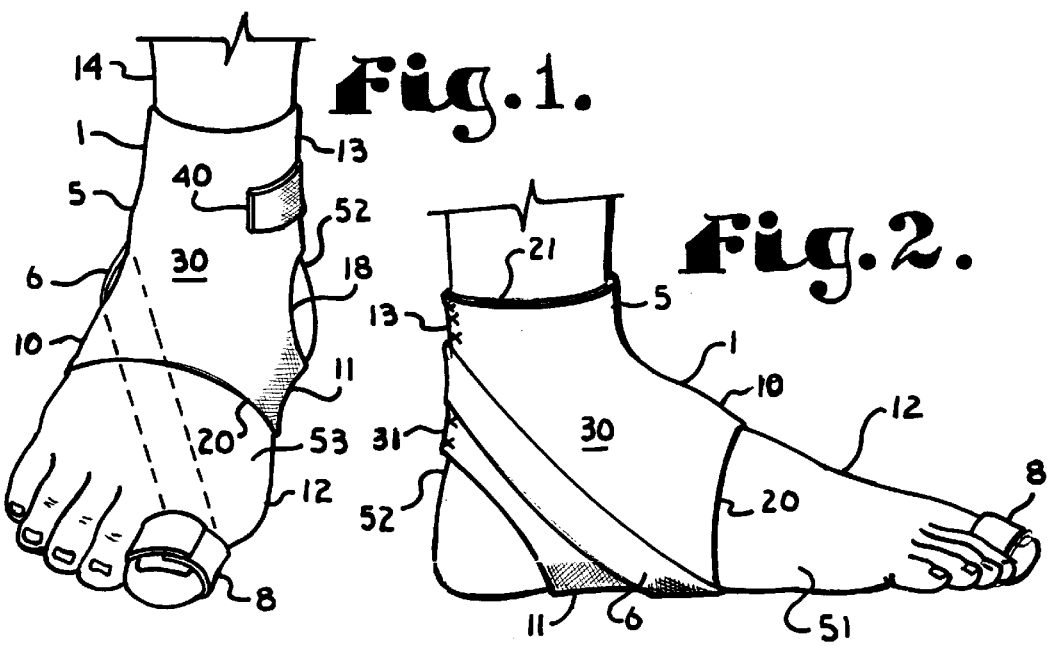
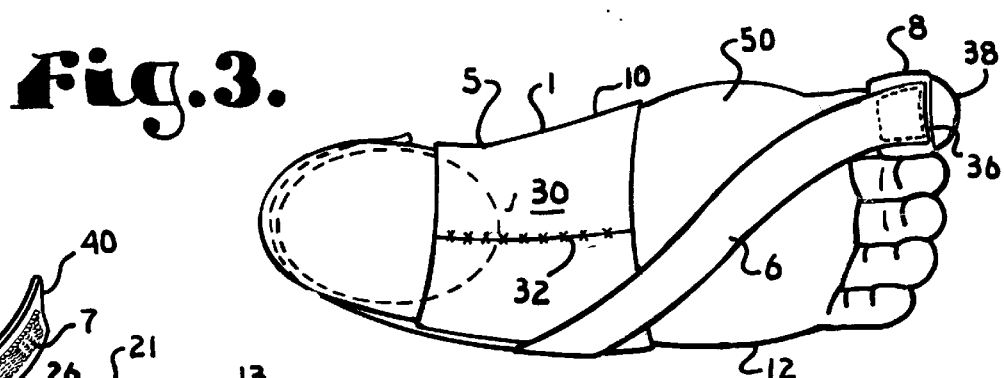
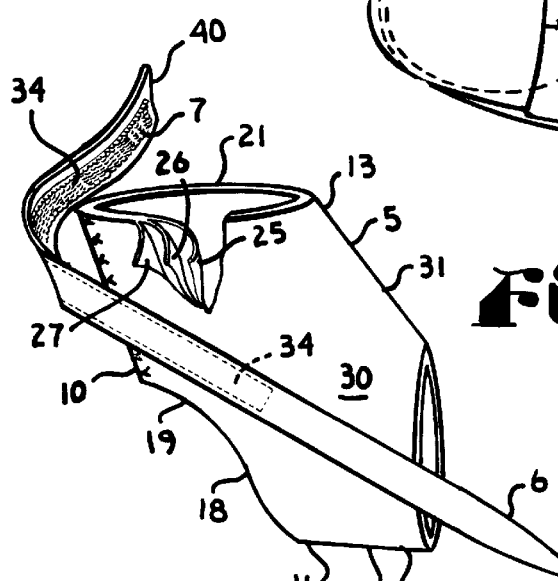

TURF TOE BRACE

CROSS REFERENCE TO RELATED APPLICATION

The present application is a continuation of U.S. Ser. No. 745,018 on a TURF TOE BRACE, filed Nov. 7, 1996, now U.S. Pat. No. 5,772,621.

BACKGROUND OF THE INVENTION

The present invention is directed to an apparatus for alleviating pain and helping to prevent exacerbation of injury due to hyper-extension of the metatarso phalangeal joint of the great toe, especially by athletes, so that the person may continue to function somewhat normally until the injury has rehabilitated.

In many athletic events and in some types of non-athletic occupations, the first metatarsophalangeal joint (MP joint) becomes injured because the great toe is suddenly hyper-extended. Such an injury stemming from a sudden hyper-extension can vary in degree, the joint capsule can be torn from the metatarsal head, articular cartilage damage can occur, or sometimes a fracture of the bone structure can occur. This injury is commonly referred to as "Turf-toe" because of its increased regularity since the introduction of artificial turf. Turf toe injuries are common in many types of athletic events such as football, soccer and basketball, especially when the athlete is forced toward the ground with the heel in the air causing the MP joint to take all of weight. Such types of injuries result from the combination of the new artificial playing surfaces and flexible types of sport footwear.

A sprain of the MP joint can be debilitating in that the great toe is very important in weight bearing, and the proximal joint must bear the brunt of every step. Turf-toe injuries can be extremely painful and typically require at least six weeks to rehabilitate. During the rehabilitation period, an athlete or worker may be in such severe pain from the injury whenever the toe extends upward that they may not be able to walk on the foot, even for normal use. Without some type of device for restricting hyper-extension, an athlete, who applies greater flexure to the toe during sporting events, is essentially unable to perform during the rehabilitation period.

Athletic trainers have devised a taping system that is utilized to secure the great toe in a plantar flexed position utilizing yoke-like strips of adhesive tape which are wrapped around the toe and secured to the foot in such a fashion to hold the toe in the plantar flexed state. By plantar flexion is meant that the toe is pulled downwardly toward the sole of the foot such that the distal tip of the great toe is urged downwardly and slightly rearwardly due to rotation relative to the remainder of the foot. By maintaining the great toe in the plantar flexed position, less stress is placed upon the supporting structures that prevent hyper-extension of the toe and pain is sufficiently prevented to the extent that the injured person can perform at least at a reduced level of ability at either athletic activities or work.

Unfortunately, the taping method of plantar flexing the big toe is very time consuming and cannot normally be accomplished by the injured person. Consequently, an athletic trainer may have to spend as much as fifteen minutes taping each injured toe and the tape is removed each day. When the person is involved in athletic events, this means that the trainer must spend a substantial amount of time for each practice session and each athletic event. Where multiple persons are injured the trainer may have insufficient time to tape the toes and also do the other activities required of the trainer. Therefore, it is desirable to provide a self applied device that relieves turf toe injury preventing or at least substantially reducing the likelihood of hyper-extension of the toe and to provide a device that can be applied relatively quickly and easily to hold the toe in the plantar flexed position.

SUMMARY OF THE INVENTION

A turf toe brace in accordance with the invention includes a sleeve or boot for placement about the foot to anchor the device and a strap that is adjustable and preferably infinitely positionable relative to the boot. The boot is constructed of a flexible material so as to fit snugly about the foot preferably encircling both the middle of the foot and the ankle region at the rear of the foot.

The strap is an elongate flexible, but generally non stretchable strip that is positionable between the great toe and the boot. One end of the strap includes a loop for encircling the great toe. The opposite end of the strap includes a fastening mechanism for releasably connecting the strap to the boot. Preferably the strap is infinitely adjustable relative to the boot. Also preferably the fastening mechanism is a hook and loop fastener with the hook portion being on one of the straps or boot and the loop portion being on the opposite. Preferably the strap extends from beneath the great toe, crosses under the foot and wraps about the rear of the foot and is connectable to the boot along a substantial length of engagement therebetween to improve the strength of connection.

The strap in use preferably extends from a loop encircling the great toe at a location beneath the foot of the user, across the bottom of the foot from near the medial side to the lateral side, upward over the lateral side of the foot, around the back of the foot and thereafter partly along the medial side of the foot.

OBJECTS AND ADVANTAGES OF THE INVENTION

Therefore, the objects of the present invention are to provide a device that substantially maintains a great toe in a plantar flexed state such that the supporting structures of the MP joint associated with the toe will not be hyper-extended during walking, running, sporting events, working and the like so as to allow the user to continue to be active during rehabilitation of the sprain; to provide such a device which is relatively easy to apply and which can be applied by the user; to provide such a device which can comparatively quickly be applied to the foot of the user; to provide such a device which is relatively low profile so as to be comfortable in use and which allows application of other support to the user's foot such as ankle taping; to provide such a device which is highly effective in alleviating pain associated with turf toe such that the user can function with at least some degree of normalcy; to provide such a device which is easy to adjust; to provide such a device including a flexible sleeve or boot for fitting about the foot of the user for anchoring the device and a strap with a toe loop such that the strap is selectively attachable to the boot and infinitely adjustable relative to that boot; and to provide such a device which is comparatively inexpensive to produce, easy to use and particularly adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a turf toe brace in accordance with the present invention shown positioned on a foot of a user.

FIG. 2 is a side elevational view of the brace shown on the foot of the user.

FIG. 3 is a bottom plan view of the brace shown on the foot of the user.

FIG. 4 is a side elevational view of the brace with a strap thereof loosened from a boot thereof and with an open toe loop.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally represents a turf toe brace in accordance with the present invention. The brace 1 includes an anchor mechanism 5, a strap 6, a fastener mechanism 7 for selectively connecting the strap to the anchor mechanism 5 and a toe loop 8 attached to the strap 6.

The anchor mechanism 5 shown in the illustrated embodiment comprises a flexible and somewhat elastic boot 10. The boot 10, includes a frontward lower sleeve 11 that is sized and shaped to snugly encircle the middle portion of a foot 12 about the arch and extend substantially therealong during use and a rearward upper sleeve 13 that is sized and shaped to encircle the rear of the foot and the lower leg of the user in the region of an associated ankle 14 during use. The boot 10 also has a heel receiving opening 18 formed by an edge 19. The lower sleeve 11 has a forward circular edge 20 and the upper sleeve 13 has an upper circular edge 21.

The boot 10 is sufficiently flexible and elastic to stretch and be manually pulled or slid over the foot 12 during application, but to also fit snugly over the foot 12 and lower leg 14 of a user once in proper position as is shown in FIGS. 1 to 3. The illustrated boot 10 is also sufficiently elastic to expand over taping (not shown here) in the region of the ankle and lower leg 14, such tape being used by athletes to strengthen or prevent injury to the ankle.

Once positioned on the foot 12, as shown in FIGS. 1 to 3, the boot 10 resists being pulled forward and functions to anchor the remainder of the brace 1. The boot 10 is removed from the foot 12 by reversing the application procedure and, in particular, by first lowering the upper sleeve 13 past the heel of the foot 12 and then pulling or sliding the entire brace 1 forward over the remainder of the foot 12.

The boot 10 is preferably constructed of three plys of material, see FIG. 4. In particular, there is an inner layer 25, a middle layer 26 and an outer layer 27. In the illustrated embodiment the inner layer 25 is a nylon-lycra mesh that is comfortable against the foot 12. The middle layer 26 is three millimeter thick neoprene. The outer layer 27 is a first component of the fastener mechanism 7 and, as illustrated, is a loop portion 30 of a hook and loop fastener of the type frequently sold under the trademark Velcro. The loop portion 30 in the illustrated embodiment covers the entire surface of the boot 10, although it is foreseen that the loop portion 30 may cover only part of the boot 10 or that a hook portion of the fastener or another type of fastener could be secured to the boot 10. The layers 25, 26 and 27 are laminated and secured together with glue or the like. The boot 10 includes seams 31 and 32 whereat a planar sheet of the laminated material of the boot is joined by stitching or the like during manufacture.

The strap 6 is constructed of an elongate strip of flexible but substantially non-stretchable material. Although many types of organic fabrics and other materials are suitable for this purpose, the illustrated strap 6 is constructed of polyester.

Mounted on one side of the strap 6 and extending substantially therealong is a hook portion 34 forming a second mating half of the fastener mechanism 7. The strap 6 and hook portion 34 are preferably sufficiently long to extend around the back of the boot 10 and partway along the medial side of the boot 10 during use, as is seen in FIG. 1, so as to strongly secure the strap 6 to the boot 10 by interengagement and connection of the loop portion 30 and hook portion 34 of the fastener mechanism 7. The strap 6 has a first end 36 operably positioned near and beneath a great toe 38 of the foot 12 during use. The strap 6 has an opposite end 40 located and attached to the medial side of the boot 10 during use. The strap 6 is easily removed from the boot 10 by pulling outward from the boot 10 starting at the strap end 40 or end 36, such that the strap 6 can be repositioned easily to apply proper tension thereto or to more comfortably position the strap 6 since the hook portion 34 will join with the loop portion 30 anywhere on virtually the entire surface of the boot 10. While there is a preferred location of the strap 6, it will vary somewhat for each person since each foot is shaped somewhat differently.

Because of the hook and loop fastener having portions 30 and 34 that is used, the strap 6 is infinitely positionable relative to the outer surface of the boot 10. Although a hook and loop fastener is utilized in the illustrated embodiment, it is foreseen that other types of fasteners, such as a buckle that is attached to the boot 10 and that receives the strap in an infinite number of fastening or tensioning positions, could be alternatively utilized in accordance with the invention. However, the hooks and loop fastener provides both the advantage of adjusting tension and allowing relocation of the strap 6 relative to the boot 10 to provide for greatest comfort.

The toe loop 8 is attached to the strap toe end 38 by stitching or the like. The illustrated loop 8 includes an elongate, flexible and generally non-stretchable strip 42 of polyester that is sized and shaped to encircle the great toe 38. The strap 42 has opposed ends 44 and 45 that are connectable by a hook portion 46 and a loop portion 47 of a hook and loop fastener so that the loop 8 fits snugly about the great toe 38 during use.

In use the brace 1 is applied by first positioning the boot 10 over the foot 12 as shown in FIGS. 1 to 3. The loop 8 of the strap 6 is then secured about the great toe 38 with the strap 6 positioned on the underside of the great toe 38 to allow tension to be applied along the strap 6 to the great toe 38 to prevent the toe 38 from raising and to hold the toe 38 in a non hyper-extended position. The strap 6 extends under a plantar or bottom side 50 of the foot 12, wraps about a lateral side 51 of the foot 12, around the rear of the foot 12 above a heel 52 thereof and then frontward over a part of a medial side 53 of the foot 12. The strap 6 is drawn sufficiently tight against the juncture thereof with the great toe 38 prior to fastening the fastener mechanism 7 so as to hold the toe 38 in the desired position and to prevent hyper-extension thereof. The strap 6 is then allowed to contact the boot 10 so that the portions 30 and 34 of the fastener mechanism 7 connect and fasten thereby holding the strap 6 in the desired position until the strap 6 is later removed by reversing the process. The brace 1 is reusable many times.

It is foreseen that other types of anchor mechanisms could be used in conjunction with the invention. For example, a lace up type jacket.

It is to be understood that while certain forms of the present invention have been illustrated and described herein, it is not to be limited to the specific forms or arrangement of parts described and shown.

What is claimed and desired to be secured by Letters Patent is as follows:

1. A turf toe brace to reduce the likelihood of hyper-extension of the great toe comprising:
   a) an anchor mechanism adapted to be secured to the foot rearwardly of the great toe; said anchor mechanism comprising a sleeve sized and shaped to be adapted to be positioned around a leg of a user and about a rear of the foot
   b) an elongate relatively non-stretchable strap;
   c) a fastening mechanism selectively attaching said strap to said anchor mechanism and being releasable from said anchor mechanism to allow adjustment of said strap relative to said anchor mechanism; and
   d) a loop located near a frontward end of said strap and adapted to be positioned around the great toe; said loop and strap being configured, such that subsequent to positioning said loop about the great toe, a first end of said strap is positioned beneath the foot in the vicinity of the great toe and said strap is sized and shaped to extend rearwardly beneath the foot when said brace is placed on the foot.

2. The brace according to claim 1 wherein:
   a) said anchor mechanism is a flexible boot including said sleeve and being adapted to encircle a portion of a foot of a user.

3. The brace according to claim 2 wherein:
   a) said boot is elastic and said sleeve is adapted to be received snugly over a foot of the user.

4. The brace according to claim 3 wherein:
   a) said sleeve is a first sleeve sized and shaped to fit over and extend behind a rear of the foot; and including
   b) a second sleeve sized and shaped to be received over and encircle the middle of the foot substantially along the arch of the foot.

5. The brace according to claim 1 wherein:
   a) said loop is fixedly attached to said strap near one end thereof.

6. The brace according to claim 5 wherein:
   a) said loop includes a flexible strip having opposite ends; said strip ends being releasably joinable together so as to fit snugly about a great toe of the user.

7. The brace according to claim 6 wherein:
   a) said strip ends are joinable by a hook and loop fastener.

8. The brace according to claim 5 wherein:
   a) said strap is sized, shaped and configured to extend from said loop beneath a great toe of a user in a manner to cross a bottom of a user's foot and thereafter extend over at least a portion of a lateral side of a user's foot while being connected to said anchor mechanism.

9. The brace according to claim 1 wherein:
   a) tension on said strap is infinitely adjustable through connection of said strap to said boot.

10. The brace according to claim 9 wherein:
    a) said fastening mechanism allows connection of said strap to said boot over a substantially large area of an exterior surface of said boot so as to allow an infinite member of possible positions of said strap to said boot so as to adjust tension and provide comfort to a user.

11. A turf toe brace to reduce the likelihood of hyper-extension of the great toe comprising:
    a) an anchor mechanism adapted to be secured to the foot rearwardly of the great toe; said anchor mechanism being a flexible boot adapted to encircle a portion of a foot of a user;
    b) an elongate relatively non-stretchable strap;
    c) a fastening mechanism selectively attaching said strap to said anchor mechanism and being releasable from said anchor mechanism to allow adjustment of said strap relative to said anchor mechanism;
    d) a loop located near a frontward end of said strap and adapted to be positioned around the great toe; said loop and strap being configured, such that subsequent to positioning said loop about the great toe, a first end of said strap is positioned beneath the foot in the vicinity of the great toe and said strap is sized and shaped to be adapted to extend rearwardly beneath the foot when said brace is placed on the foot;
    e) said boot is elastic and includes a sleeve that is adapted to be received snugly over a foot of the user;
    f) said sleeve is a first sleeve sized and shaped to fit over and extend behind a rear of the foot; and including
    g) a second sleeve sized and shaped to be received over and encircle the middle of the foot substantially along the arch of the foot.

\* \* \* \* \*